(12) United States Patent
Avnery (10) Patent No.: US 6,702,984 B2
(45) Date of Patent: Mar. 9, 2004

(54) DECONTAMINATION APPARATUS

(75) Inventor: Tzvi Avnery, Winchester, MA (US)

(73) Assignee: Advanced Electron Beams, Inc., Wilmington, MA (US)

( * ) Notice: Subject to any disclaimer, the term of this patent is extended or adjusted under 35 U.S.C. 154(b) by 0 days.

(21) Appl. No.: 10/021,827

(22) Filed: Dec. 13, 2001

(65) Prior Publication Data

US 2002/0110481 A1 Aug. 15, 2002

Related U.S. Application Data (60) Provisional application No. 60/255,308, filed on Dec. 13, 2000.

(51) Int. Cl.[7] ................................. A61L 2/00
(52) U.S. Cl. .................. 422/22; 250/455.11; 422/1; 422/23
(58) Field of Search ................ 422/1, 22, 23; 250/455.11

(56) References Cited

U.S. PATENT DOCUMENTS

| | | | |
|---|---|---|---|
| 3,780,308 A | 12/1973 | Nablo | 250/492 |
| 4,652,763 A | 3/1987 | Nablo | 250/492.3 |
| 5,136,212 A | 8/1992 | Eguchi et al. | 315/150 |
| 5,378,898 A | 1/1995 | Schonberg et al. | 250/492.3 |
| 5,457,269 A | 10/1995 | Schonberg | 588/212 |
| 5,530,255 A | 6/1996 | Lyons et al. | 250/492.3 |
| 5,539,212 A | 7/1996 | Matthews et al. | 250/492.3 |
| 5,561,298 A | 10/1996 | Cirlin et al. | 250/432 R |
| 5,603,853 A | 2/1997 | Mombo-Caristan | 219/121.64 |
| 5,709,842 A | 1/1998 | Held et al. | 422/292 |
| 5,744,811 A | 4/1998 | Schonberg et al. | 250/492.3 |
| 5,882,487 A | 3/1999 | Li et al. | 204/157.41 |
| 5,962,995 A | 10/1999 | Avnery | 315/506 |
| 5,998,691 A | 12/1999 | Abel et al. | 588/200 |
| 6,054,714 A | 4/2000 | Izutsu et al. | 250/492.3 |
| 6,113,851 A | 9/2000 | Soloshenko et al. | 422/22 |
| 6,140,657 A | 10/2000 | Wakalopulos et al. | 250/492.3 |
| 6,203,755 B1 * | 3/2001 | Odland | 422/22 |
| 6,264,836 B1 | 7/2001 | Lantis | 210/188 |

FOREIGN PATENT DOCUMENTS

JP  11137645  5/1999

* cited by examiner

Primary Examiner—Krisanne Thornton
(74) Attorney, Agent, or Firm—Hamilton, Brook, Smith & Reynolds, P.C.

(57) ABSTRACT

An apparatus and method of decontaminating surfaces on a living creature. A beam of electrons is generated with an electron beam generator operating in the range of about 40 kv to 60 kv. The beam of electrons exit the electron beam generator through an exit window. The surfaces on the living creature are irradiated with the beam of electrons. The beam of electrons are of an energy sufficient to decontaminate the surfaces without damaging living tissue.

55 Claims, 7 Drawing Sheets

FIG. 9

DECONTAMINATION APPARATUS

RELATED APPLICATIONS

This application claims the benefit of U.S. Provisional Application No. 60/255,308, filed on Dec. 13, 2000. The entire teachings of the above application are incorporated herein by reference.

BACKGROUND

Personnel working within environments contaminated with hazardous chemical or biological agents typically wear protective suits to prevent direct exposure to the hazardous agents. Since the outer surfaces of the suit can become covered with the hazardous agents during use, the user is in danger of becoming contaminated when the time comes to remove the suit. Therefore, it is apparent that there are instances where the skin and inner clothing of such personnel can come into contact with the hazardous agents. In addition, there may be situations where people not wearing protective clothing find themselves in a contaminated environment and become contaminated with such hazardous agents.

SUMMARY

The present invention is directed to a decontamination apparatus and method of decontaminating which is suitable for decontaminating surfaces, including clothing or the skin on a person, or other living creatures. Decontaminating surfaces on a living creature includes generating a beam of electrons with an electron beam generator operating in the range of about 40 kv to 60 kv. The beam of electrons exit the electron beam generator through an exit window. The surfaces on the living creature are irradiated with the beam of electrons. The beam of electrons are of an energy sufficient to decontaminate the surfaces without damaging living tissue.

In preferred embodiments, ozone is reduced in front of the exit window with an ozone reduction system. In one embodiment, the ozone reduction system includes a gas removal system for removing ozone generated in front of the exit window. In another embodiment, the ozone reduction system includes a nozzle assembly for providing inert gas to occupy an area adjacent to the exit window to prevent the generation of ozone. The nozzle assembly is arranged around the exit window and directs the gas in substantially the same direction as the beam of electrons. The inert gas can be a low density gas such as helium which increases the range of the electrons. When low density gas is employed, the exit window of the electron beam generator can be spaced between about ¼ to an 1 inch away from the surfaces. The electron beam generator commonly operates at 50 kv and lower with 40 kv to 50 kv being typical, and wherein the exit window of the electron beam generator is spaced between about ¼ to ½ inches away from the surfaces. The electron beam generator can be moved with a robotic arm for moving the beam of electrons over the surfaces. Typically, the exit window is spaced from the surfaces with a spacing device which can be a sensor.

The present invention is also directed to decontaminating surfaces on a living creature including generating beams of electrons from a series of electron beam generators operating in the range of about 40 kv to 60 kv and positioned to face multiple surfaces on the living creature. The multiple surfaces on the living creature are simultaneously irradiated with the beams of electrons. The beams of electrons are of an energy sufficient to decontaminate the surfaces without damaging living tissue.

The present invention is also directed to decontaminating surfaces including generating a beam of electrons with an electron beam generator. The beam of electrons exit the electron beam generator through an exit window to irradiate the surfaces. A supply of low density gas is provided to occupy an area adjacent to the exit window to increase the range of the beam of electrons. The exit window of the electron beam generator is actively spaced an effective distance away from the surfaces with a spacing device.

The present invention is also directed to a decontamination apparatus including an electron beam generator operating in the range of about 40 kv to 60 kv for generating a beam of electrons to decontaminate surfaces. The beam of electrons exit the electron beam generator through an exit window. A nozzle assembly provides a supply of low density gas for occupying an area adjacent to the exit window to increase the range of the beam of electrons. A spacing device spaces the exit window of the electron beam generator between about ¼ to 1 inch away from the surfaces.

In preferred embodiments, the surfaces are often on a living creature, and the low density gas is helium. The nozzle assembly is arranged around the exit window and directs the gas in substantially the same direction as the beam of electrons. The electron beam generator commonly operates at 50 kv and lower, with 40 kv to 50 kv being typical, and wherein the spacing device spaces the exit window of the electron beam generator between about ¼ to ½ inches away from the surfaces. The electron beam generator can be mounted to a robotic arm for moving the beam of electrons over the surfaces. If desired, more than one electron beam generator can be mounted to the robotic arm.

The present invention is also directed to a decontamination apparatus including a series of electron beam generators operating in the range of about 40 kv to 60 kv for generating beams of electrons to decontaminate multiple surfaces of a living creature. The beams of electrons exit the electron beam generators through respective exit windows. The electron beam generators are configured for simultaneously irradiating the multiple surfaces of the living creature with the electron beams. A nozzle assembly provides a supply of low density gas for occupying areas adjacent to the exit windows to increase the range of the beam of electrons.

The present invention is further directed to a decontamination apparatus including an electron beam generator for generating a beam of electrons to decontaminate surfaces. The beam of electrons exits the electron beam generator through an exit window. An ozone reduction system reduces ozone in front of the exit window. A spacing device actively spaces the exit window of the electron beam generator within an effective distance away from the surfaces.

When the power of the electron beam generator in the present invention is selected to be relatively low, the beam of electrons has sufficient energy to decontaminate the outer layers of dead skin of a person but not enough energy to penetrate deep enough to reach or damage living tissue. In addition, by forming an area of low density helium gas adjacent to the exit window, the density of gases in front of the exit window is reduced. This provides increased range for the low power beam of electrons resulting in more effective decontamination.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENTS

Figure 1:
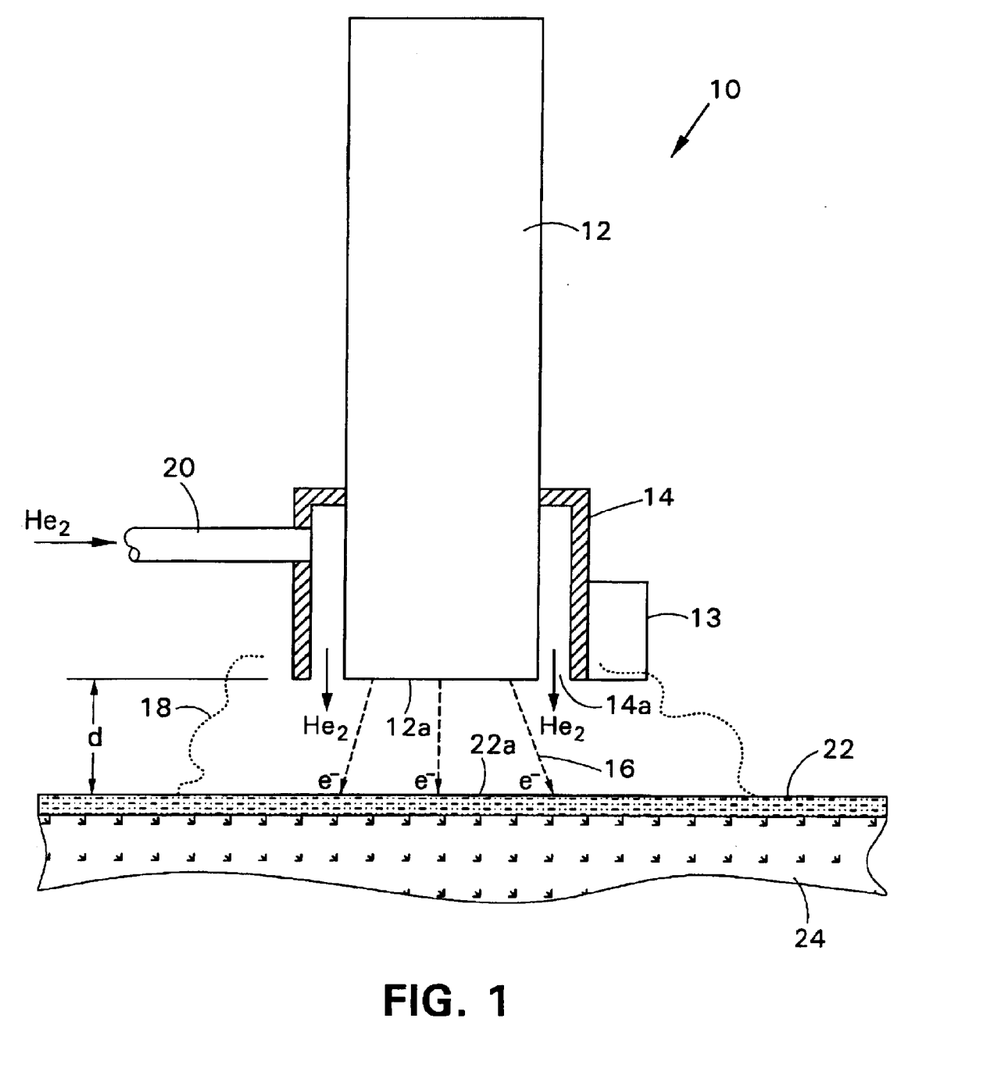
FIG. 1 is a schematic drawing of the present invention decontamination apparatus irradiating a section of skin, with the nozzle assembly shown in section.

Referring to FIG. 1, electron beam irradiation or decontamination apparatus 10 is employed for decontaminating surfaces having hazardous agents thereon and is suitable for decontaminating the clothes and skin of humans, as well as other living creatures. Decontamination apparatus includes an electron beam generator 12 for producing a low power beam 16 of electrons e$^-$ which exit the electron beam generator 12 through an exit window 12a. A nozzle assembly 14 is mounted to electron beam generator 12 and concentrically surrounds the exit window 12a. Nozzle assembly 14 is provided with an inert low density gas such as helium (He$_2$) from a supply line 20. Nozzle assembly 14 directs a curtain of the gas from outlet 14a which flows in substantially the same direction as the beam 16 of electrons e$^-$. This produces a volume of low density gas 18 adjacent to and in front of the exit window 12a. Depending upon the flow rate of the gas and the proximity of electron beam generator 12 to the surface 22a to be irradiated, the volume of gas 18 may extend from the exit window 12a to the surface 22a as shown, to occupy the space therebetween. The volume of low density gas 18 increases the range of the beam 16 of electrons e$^-$ and allows the beam 16 of electrons e$^-$ to travel about seven times further than the distance obtainable when traveling through higher density air. Consequently, electron beam generator 12 can be of a low power, about 60 kv or less, with the electrons e$^-$ capable of reaching the surface 22a to be irradiated from distances that ordinarily would be too far away.

Often, the surface 22a is a person's skin requiring decontamination from hazardous agents such as chemicals or biological agents (bacteria, viruses, etc.). The beam 16 of electrons e$^-$ attacks the hazardous agents and renders them harmless. In the case of hazardous chemicals, the electron beam 16 converts the hazardous chemicals into harmless substances by causing chemical reactions. In the case of biological agents such as organisms, bacteria or viruses, the electron beam 16 kills the organisms, bacteria or viruses by disabling or destroying cellular structures. Since the electron beam 16 has low power of 60 kv or less, the electrons e$^-$ penetrate and treat only the outer layer of dead skin 22 which is about 10 to 40 mm thick. Most x-rays generated are of low power and are also stopped at the outer layer of dead skin 22. The electrons e$^-$ generated by an electron beam generator 12 operating at 60 kv or less have enough energy to decontaminate surface 22a but do not have enough energy to penetrate into the living epidermis 24, so that the living tissue experiences little or no damage. In addition, at such low power, the generation of x-rays is kept to a minimum.

When used for decontaminating living creatures such as people, electron beam generator 12 is preferably operated at 60 kv or less (usually 50 kv or less), with 40 kv to 50 kv being the typical range. At such voltages, typically the exit window 12a of electron beam generator 12 is positioned a distance "d" of about ¼ to ½ inches away surface 22a with distances "d" of up to about 1 inches sometimes being possible, but more commonly possible when electron beam generator 12 is operated at about 60 kv. If the volume of gas 18 was not employed, the exit window 12a of electron beam generator 12 would normally have to be a maximum of about ⅛ inch away from surface 22a in order for the beam 16 of electrons e$^-$ to pass through the air to reach surface 22a with sufficient energy for decontamination. A distance "d" of ⅛ inch is sometimes not practical for use on living creatures. The reason for this is that some living creatures have some surfaces that include curved and complex structures. Some of these structures have configurations with protrusions or recessed areas which prevent the electron beam generator 12 from being within ⅛ inches away from portions of the surfaces to be irradiated. Examples of such structures are the ears, nose, between the toes, etc., of some creatures. By having the increased range for the low power beam 16 of electrons e$^-$, such difficult areas can be irradiated sufficiently for decontamination with little or no tissue damage. In other typical applications, decontamination apparatus 10 can be used to decontaminate the clothing of a person or the outer surfaces of a protective suit while worn by the user. When decontaminating clothes on a person, the clothes sometimes have wrinkles and folds in the material which form recesses or crevasses. The increased range of the low power beam 16 of electrons e$^-$ allow such crevasses to be sufficiently irradiated for decontamination.

The inert low density gas 18 in front of the exit window 12a also provides inerting in the region of the beam 16 of electrons e$^-$ to reduce or eliminate the formation of ozone (O$_3$). Ozone is typically formed by the interaction of the beam 16 of electrons e$^-$ with oxygen (O$_2$) in the air and can be harmful if inhaled. Replacing the air in front of the exit window 12a with the inert gas 18 removes oxygen from the region which would have formed ozone.

Typically, electron beam generator 12 is a compact, hermetically sealed unit and can be similar to those disclosed in U.S. Pat. No. 5,962,995, U.S. patent application Ser. No. 09/349,592, filed Jul. 9, 1999, and U.S. patent application Ser. No. 09/209,024, filed Dec. 10, 1998, the contents of which are incorporated herein by reference in their entirety. Electron beam generator 12 is commonly in the range of about two inches in diameter and six to eight inches long for units operating in the range 40 kv to 60 kv. Alternatively, other suitable electron beam generators can be employed. Although nozzle assembly 14 is shown in FIG. 1 to surround the exit window 12a of electron beam generator 12, alternatively, the nozzle assembly 14 can be positioned adjacent to the electron beam generator 12. In addition, nozzle assembly 14 does not have to direct the low density gas 18 in the same direction as the electron beam 16 but instead can direct the gas 18 perpendicularly or at an angle to the electron beam 66.

Figure 2:
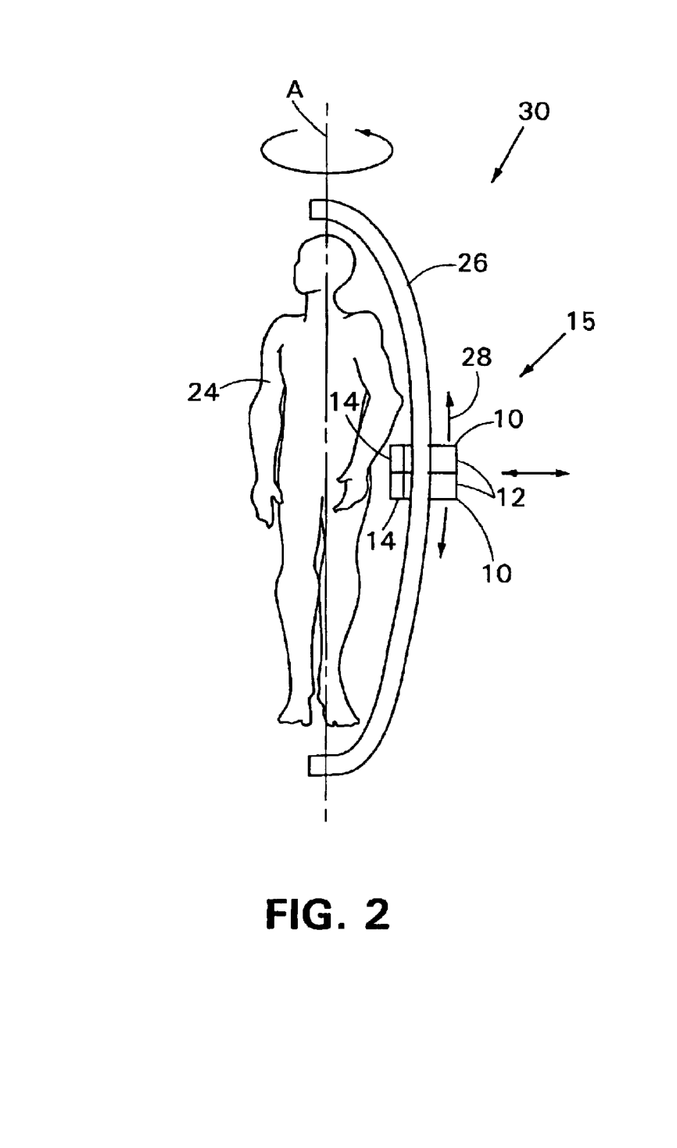
FIG. 2 is a schematic drawing of an embodiment of the present invention for irradiating a person's body.

In order to irradiate the entire body 24 of a person, decontamination apparatus 10 can be part of a decontamination apparatus 30 where the decontamination apparatus 10 forms an electron beam generator irradiation unit 15 that is mounted on a robotic arm 26, as shown in FIG. 2. The robotic arm 26 moves decontamination apparatus 10 around the body 24 for providing complete irradiation coverage. Additionally, more than one decontamination apparatus 10 can be mounted to robotic arm 26, as shown, to form the electron beam generator irradiation unit 15 in order to provide a larger irradiation region for obtaining a faster decontamination time. The robotic arm 26 may rotate around the body 24 about an axis A while vertically translating the irradiation unit 15 on a track up and down as shown by arrows 28. Typically, irradiation unit 15 is incrementally translated in the vertical direction after each rotation of robotic arm 26 around body 24 until the entire body 24 is irradiated. The irradiation unit 15 can also be translated laterally inwardly and outwardly relative to the body 24 to maintain the desired distance "d" between the exit windows 12a of the electron beam generators 12 and the surfaces of the body 24 in view that the surfaces of body 24 have variable distances from robotic arm 26. The irradiation unit 15 can be tilted in order to be properly orientated relative to the changing surfaces of body 24. In cases where there is more than one electron beam generator 12, the electron beam generators 12 can be independently translated laterally. The distance "d" can be continuously and actively controlled by a spacing device 13 (FIG. 1) mounted to each electron beam generator 12. In one embodiment, the spacing device 13 is a proximity sensor which controls the lateral translation of the associated decontamination apparatus 10. Although arm 26 is shown in FIG. 2 to rotate about axis A, alternatively, arm 26 may be stationary while vertically translating irradiation unit 15, in which case, the person stands on a rotary table that spins the body 24 about axis A.

Figure 3:
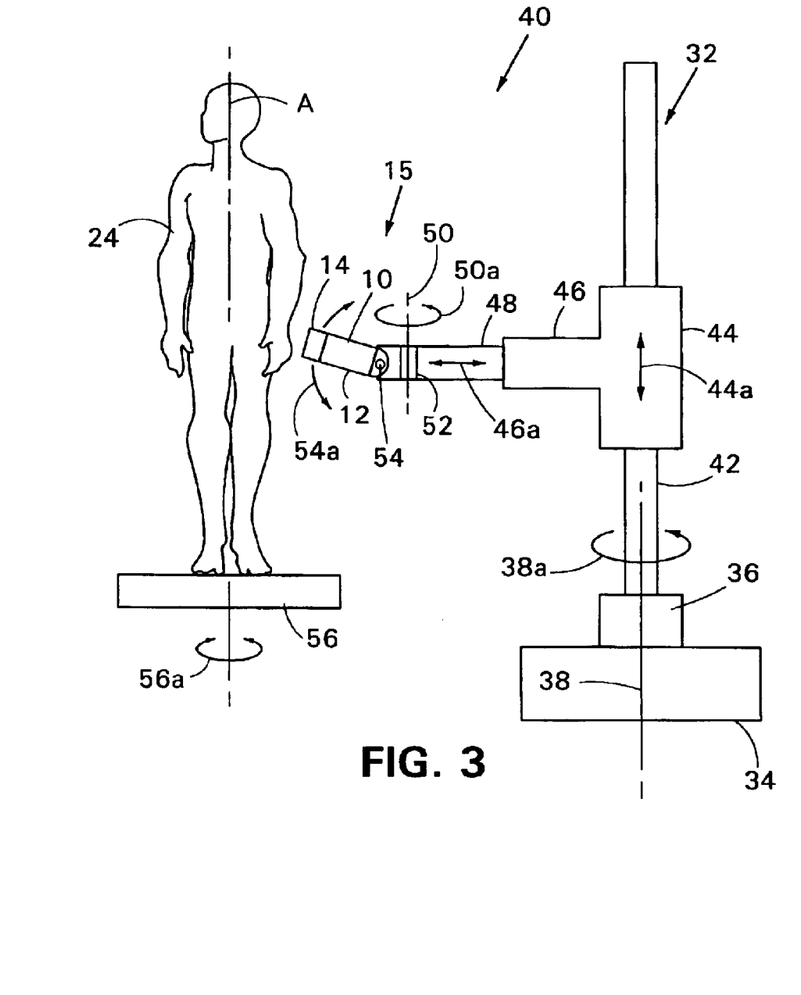
FIG. 3 is a schematic drawing of another embodiment of the present invention.

Referring to FIG. 3, decontamination apparatus 40 is another embodiment of the present invention in which the irradiation unit 15 is mounted to a conventional type robotic arm 32. As with decontamination apparatus 30, irradiation unit 15 can include one or more decontamination apparatuses 10. Robotic arm 32 includes a series of linear and rotating joints which allow the irradiation unit 15 to move over the surfaces of a person's body 24 for decontamination purposes. The robotic arm 32 shown in FIG. 3 includes a waist joint 36 rotatably mounted to a fixed base 34 about a vertical axis 38 for rotation in the direction of arrows 38a. A vertical post 42 extending along vertical axis 38 is mounted to waist joint 36. A shoulder joint 44 is mounted to post 42 for linearly translating vertically up and down the post 42 in the direction of arrows 44a. An arm 48 is mounted to the shoulder joint 44 for linearly translating laterally relative to shoulder joint 44 within portion 46 in the direction of arrows 46a. Arm 48 includes a first rotational joint 52 for rotation about axis 50 in the direction of arrows 50a and a second rotational joint 54 for rotation in the direction of arrows 54a about an axis that is perpendicular to axis 50. Irradiation unit 15 is distally mounted to arm 48 beyond joint 54. Waist joint 36 laterally pivots arm 48 and shoulder joint 44 raises and lowers arm 48 relative to body 24. Arm 48 translates irradiation unit 15 towards and away from body 24 within portion 46 of shoulder joint 44. Joints 52 and 54 pivot irradiation unit 15 relative to body 24.

As with decontamination apparatus 30, irradiation unit 15 is continuously and actively maintained at the desired distance "d" from the surfaces of body 24 by spacing device 13 while being maneuvered around body 24. If desired, the body 24 can stand on a rotary table 56 which rotates body 24 about axis A in the direction of arrows 56a. If a rotary table 56 is employed, the decontamination process can be accomplished more quickly. It is understood that the robotic arm 32 shown in FIG. 3 is an example of a robotic arm that can be employed, and that many other suitable variations or alternative robotic arms are possible. For example, joints can be added to or omitted from robotic arm 32. One such example is replacing shoulder joint 44 with a rotating joint that raises and lowers arm 48. Another example is combining joints 52 and 54 into a single joint. In addition, another linear joint for movement orthogonal to those depicted by arrows 46a and 44a can be added.

Figure 4:
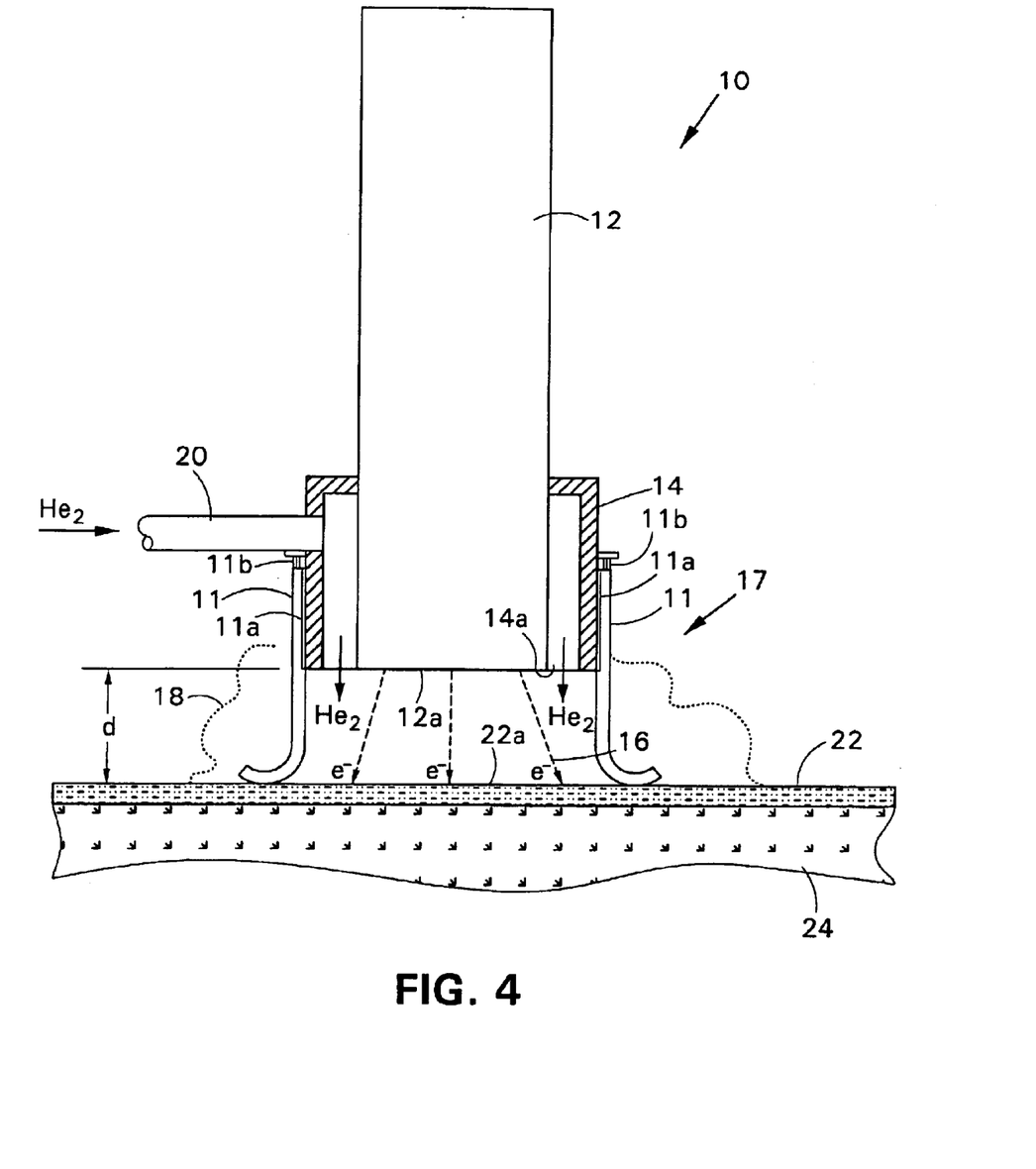
FIG. 4 is a schematic drawing of the present invention decontamination apparatus having a mechanical spacing device.

Referring to FIG. 4, decontamination apparatus 10 can include a mechanical spacing device 17 that includes one or more protrusions 11 mounted to the electron beam generator 12. Typically, the protrusions 11 are fixed to the nozzle assembly 14 and continuously and actively provide the proper distance "d" between the exit window 12a and the surface 22a by contacting the surface 22a. The distal ends of protrusions 11 can be curved as shown or can be straight. The mechanical spacing device 17 can be employed with a robotic arm 26/32 or can be employed when decontamination apparatus 10 is used as a hand held device. When mounted to a robotic arm 26/32, the mechanical spacing device 17 can also include pressure sensing elements 11a associated with the protrusions 11 for controlling the force at which the robotic arm presses the protrusions 11 against the surface 22a. In FIG. 4, the sensing elements 11a are shown to be fixed between protrusions 11 and nozzle assembly 14 to sense shear forces therebetween. Alternatively, protrusions 11 can press axially against a set of sensing elements 11b for sensing axial force. In addition, protrusions 11 can be spring load either vertically or pivotally for tripping a limit switch. Although multiple protrusions 11 have been shown in FIG. 4 to form spacing device 17, alternatively, spacing device 17 can also be formed by a single annular projection or hood. The hood may include slots or openings therethrough to allow the escape of gases.

When employed as a hand held device, decontamination apparatus 10 may include radiation shields for added protection and more than one decontamination apparatus 10 can be employed to form the irradiation unit 15. It is also understood if hand held, that decontamination apparatus 10 can employ either the mechanical spacing device 17 or the spacing device 13 depicted in FIG. 1, where the spacing device 13 is a proximity sensor. The proximity sensor can be connected to a distance indication system such as a speaker and/or an indicator light to provide an audible tone and/or a visible light when the proper distance "d" is obtained. The distance indication system can also include a distance meter or distance readout. The spacing devices 13/17 along with any associated equipment can be considered a spacing system.

Figure 5:
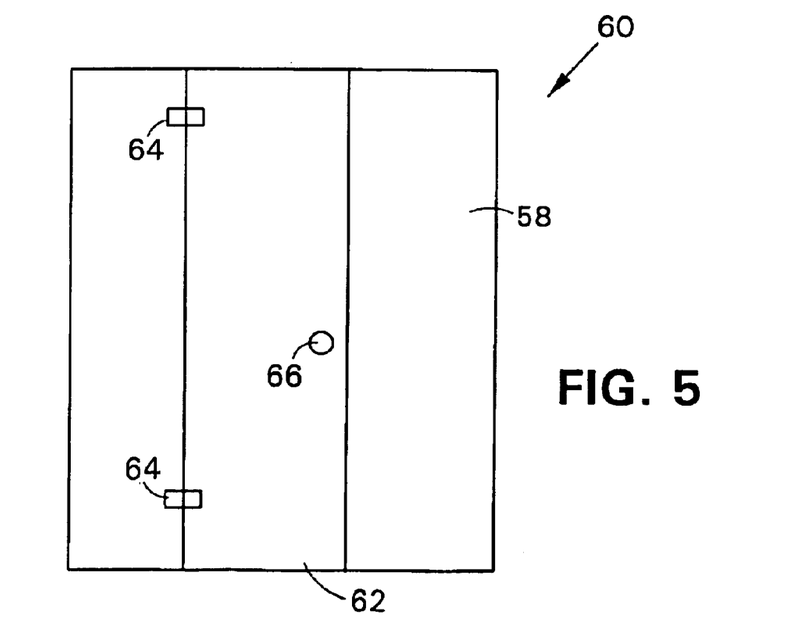
FIG. 5 is a front view of still another embodiment of the present invention.
Figure 6:
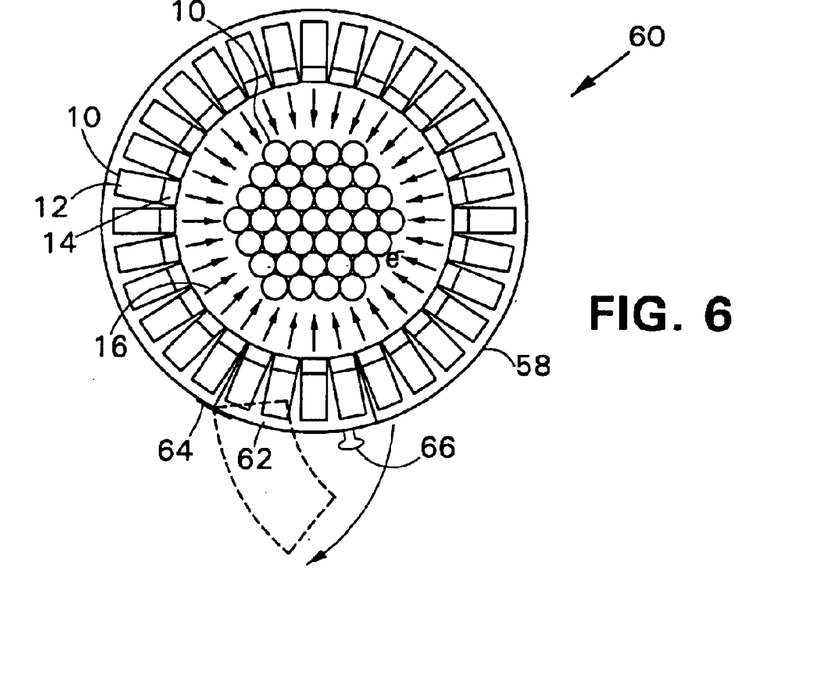
FIG. 6 is a plan schematic view of the embodiment depicted in FIG. 5 with the top removed.

Referring to FIGS. 5 and 6, decontamination apparatus 60 is still another embodiment of the present invention. Decontamination apparatus 60 includes an enclosure 58 containing a series of decontamination apparatuses 10 that are arranged to provide substantially uninterrupted electron beam coverage from the multiple surfaces of a body 24 standing within enclosure 58. Many of the surfaces of body 24 face on different directions. Some of the surfaces of body 24 are curved or angled relative to each other, or are on opposite sides of body 24, etc. A first lateral series of decontamination apparatuses 10 are arranged abutting each other and facing inwardly. This forms an enclosed lateral wall of electron beam generators 12 to generate a substantially continuous laterally directed wall or curtain of electron beams 16 inwardly into the enclosure 58 from substantially all sides or directions. In addition, a second vertical series of abutting decontamination apparatuses 10 are positioned at the bottom and the top of enclosure 58 for forming a floor and ceiling of electron beam generators 12 to generate a substantially continuous vertical shower of electron beams from axial ends of enclosure 58. Each decontamination apparatus 10 may be individually moveable inwardly and outwardly relative to the space within enclosure 58 for providing the proper distance "d" between the exit windows 12a of the electron beam generators 12 and the surfaces of a body 24. Spacing devices 13 or 17 can be employed for controlling the distance "d". Decontamination apparatus 60 is able to provide simultaneous irradiation of the surfaces of the entire body 24 from multiple directions, thereby providing fast or rapid decontamination.

In some cases, irradiation can be sequentially performed by decontamination apparatus 60 where only a portion of the electron beam generators 12 are irradiating at a given time. For example, the irradiation can be started at one part of the body 24, such as the head, and then the remaining electron beam generators 12 incrementally activated until the entire body 24 is irradiated. This may be helpful to prevent claustrophobia where only portions of the electron beam generators 12 are moved into position for irradiation at a given time. The electron beam generators 12 could be moved into position to irradiate as much as ¼ to ½ of the body 24 at the same time.

Entry into enclosure 58 is provide by a door 62 having a handle 66 and hinges 64. Alternatively, other suitable doors can be employed. For example, the longitudinal axis of enclosure 58 can be horizontal so that the door is at one axial end and the body 24 is inserted therein while lying horizontally. In such a design, a horizontal support may be provided for supporting the body 24 without blocking the electron beams 16. Although enclosure 58 is shown to be cylindrical in shape, alternatively, enclosure 58 may have a cross section that is rectangular, oval, polygonal, or combinations thereof. The enclosure 58 can also have an interior shape closely resembling a human shape. In addition, it is understood that the number of electron beam generators 12 employed is determined by the size of enclosure 58 and the size of the individual electron beam generators 12. Furthermore, decontamination apparatus 60 can be configured so that only a portion of body 24 is simultaneously irradiated, for example, half the body 24, which then is turned for irradiation of the other half. A rotary table 56 (FIG. 3) can be employed.

In the present invention, since the electron beam generators 12 can be made small in size, in some cases the electron beam generators 12 are able to maneuver close enough to the surfaces to be irradiated to provide sufficient decontamination without the use of the low density gas 18 and without damaging living tissue when irradiating skin. Although irradiation through air when an inert gas is not supplied results in the formation of ozone, if irradiation of a body 24 of a person can be performed within about 20 seconds, the person can hold his or her breath during the irradiation process to avoid inhalation of ozone. In other situations where the electron beam generators 12 are positioned closely to the surfaces to be irradiated (about ⅛ inches), a nozzle assembly 14 can be used to direct inert gases that are not necessarily low density for inerting purposes, such as nitrogen, argon, etc., to reduce or eliminate the formation of ozone.

Figure 7:
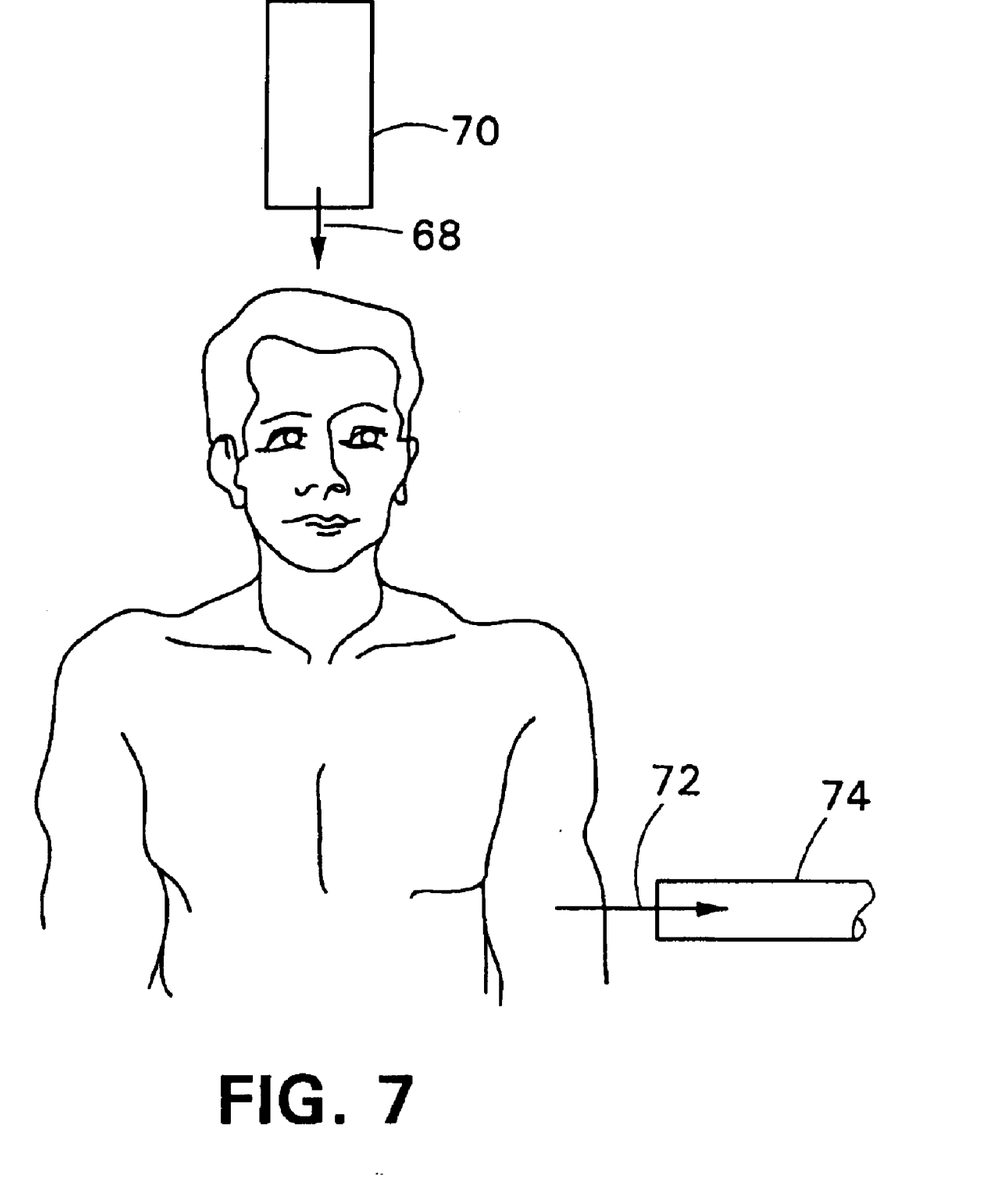
FIG. 7 is a schematic front view of an air/oxygen supply system providing a person with air or oxygen during irradiation, with gases undesirable for inhalation being removed by a gas removal system.

If the irradiation time takes longer than about 20 seconds, both when an inert gas is supplied or when irradiating through the air, the person can be provided with a supply of breathable air or oxygen 68 through an air/oxygen supply system 70, such as a nozzle assembly, from an air or oxygen supply as shown in FIG. 7. A gas removal or exhaust system 74, for example, a suction nozzle, can be provided for removing gases 72 undesirable for inhalation, such as the supplied inert gases and/or ozone. A blower system can also be employed as the gas removal system. The air/oxygen supply system 70 and the gas removal system 74 are either positioned to not interfere with the irradiation process or are movable. In some cases, the person may have to hold his/her breath initially until the head is decontaminated.

Figure 8:
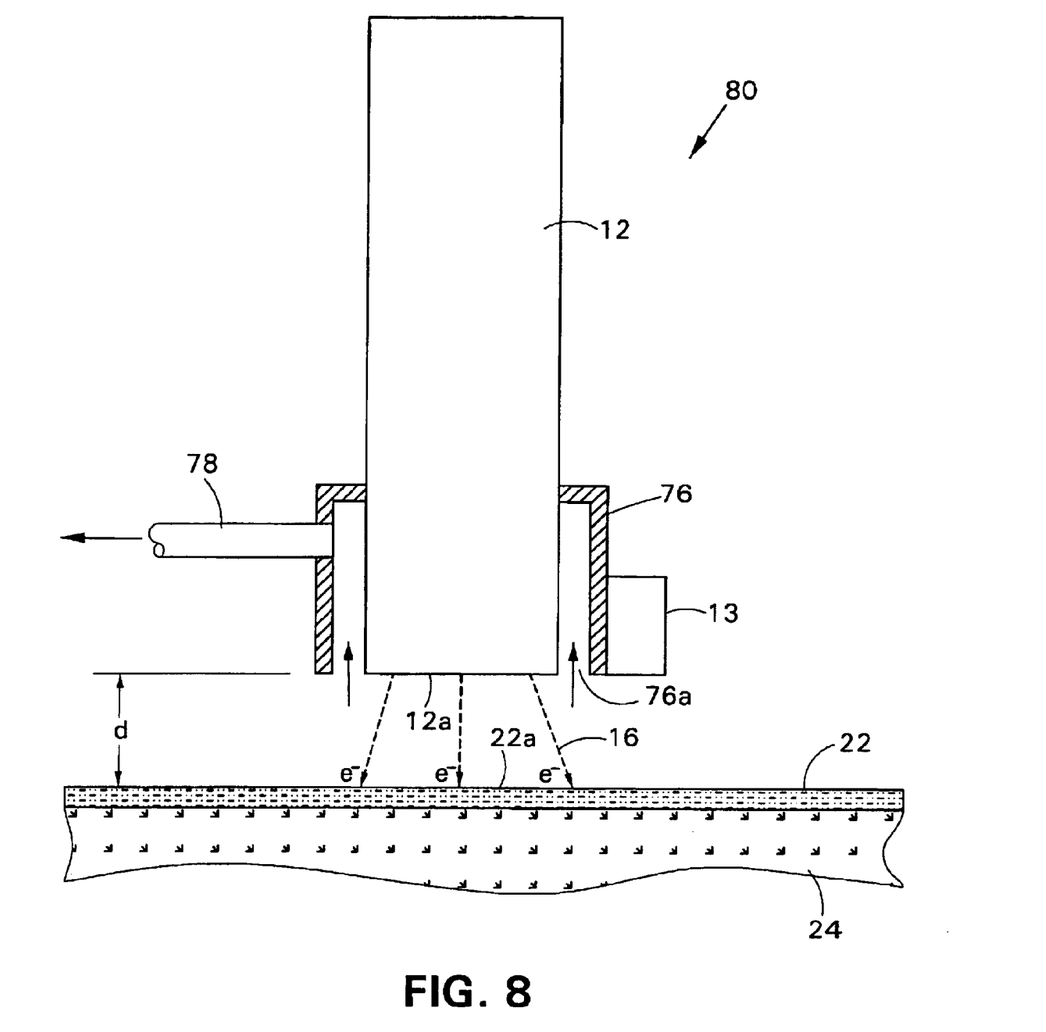
FIG. 8 is a schematic drawing of yet another embodiment of the present invention decontamination apparatus.

Referring to FIG. 8, electron beam irradiation or decontamination apparatus 80 is yet another embodiment of the present invention which differs from apparatus 10 depicted in FIG. 1 in that apparatus 80 includes a gas removal vacuum assembly 76 concentrically surrounding the exit window 12a of the electron beam generator 12 and mounted thereto. Gases including any generated ozone are drawn into the inlet 76a of vacuum assembly 76 from the region adjacent to exit window 12a, between surface 22a and exit window 12a, and then out vacuum line 78. This eliminates or reduces the amount of ozone in the region of apparatus 80. In some cases, the pressure in front of exit window 12a can be lowered, thereby increasing the range of the beam 16 of electrons $e^-$.

Figure 9:
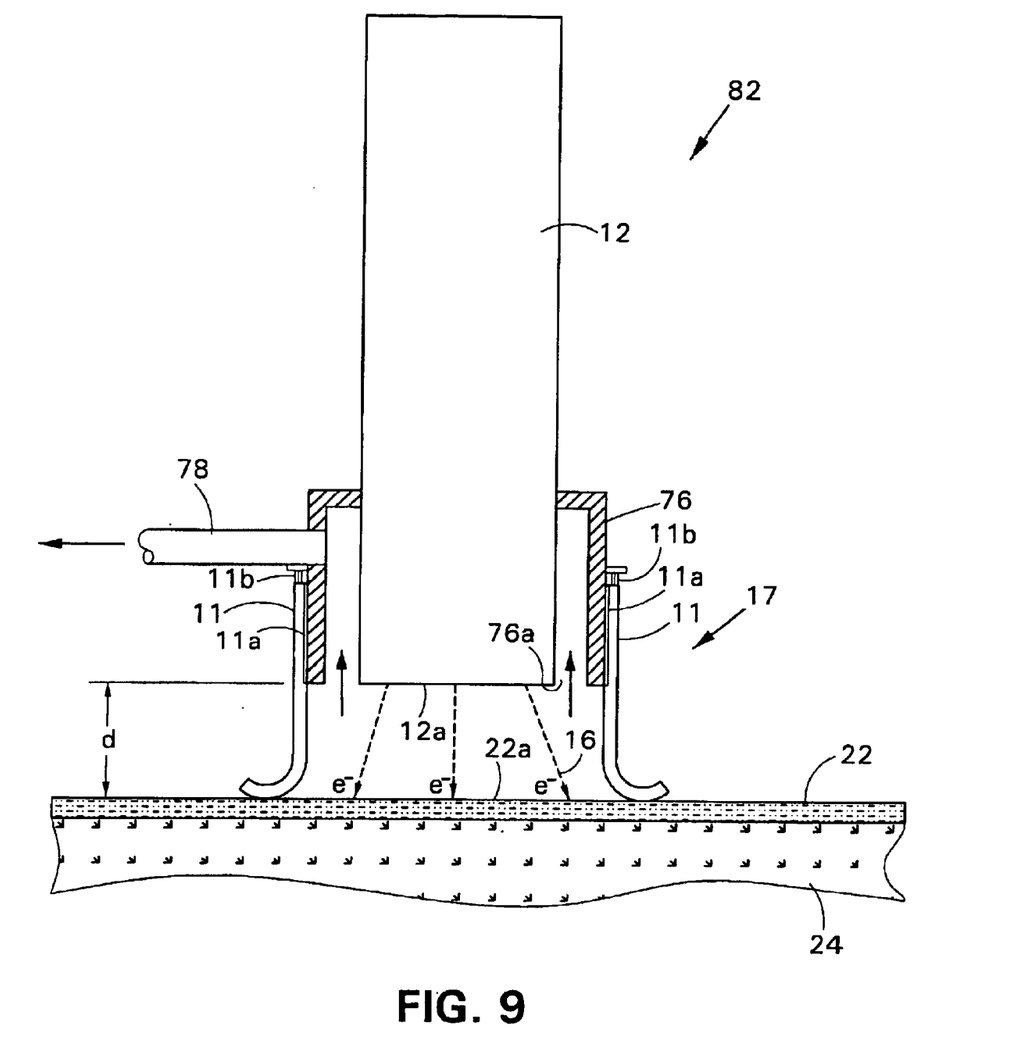
FIG. 9 is a schematic drawing of another embodiment of the present invention decontamination apparatus.

Referring to FIG. 9, electron beam irradiation or decontamination apparatus 82 is another embodiment of the present invention which differs from apparatus 10 depicted in FIG. 4 in that apparatus 82 includes the vacuum assembly 76 of FIG. 8. Typically, spacing device 17 is a hood or shroud with a single annular protrusion 11 which allows a greater decrease of the pressure in front of exit window 12a. This further increases the range of the beam 16 of electrons $e^-$, thereby increasing the distance "d" at which effective decontamination can be obtained. The protrusion 11 can be made with openings or slots therethrough to allow some flow of gases. Apparatuses 80 and 82 are typically employed without supplying inerting gases, but in some cases, providing inert gases can be desirable. The gas removal or exhaust arrangements described above as well as the supply of inerting gases can be among other things, referred to as ozone reduction systems.

While this invention has been particularly shown and described with references to preferred embodiments thereof, it will be understood by those skilled in the art that various changes in form and details may be made therein without departing from the scope of the invention encompassed by the appended claims.

For example, although the present invention decontamination apparatuses have been described for decontaminating clothing and living creatures, the decontamination apparatuses may be used for any suitable irradiation application. Such applications may include the irradiation of non-living objects, materials or substances for sterilization, curing, or facilitating chemical reactions. Furthermore, electron beam generators 12 having power higher than 60 kv or lower than 40 kv may be used. In cases where non-living objects, materials or substances are to be irradiated, electron beam generators 12 can operate well above 60 kv, for example, 125 kv or greater. The low density gas 18, when used, allows the electron beam generators 12 to be positioned farther away from the objects, materials or substances than normally possible without the low density gas. Such increased range of the beam 16 of electrons e⁻ also permits deeper penetration into the objects, materials or substances as well as more thorough irradiation of complex geometries. There may be situations when irradiating non-living objects, materials or substances in which supplying other inert gases is desirable. Also, the removal of gases with a gas removal system may be desirable. It is understood that features of the different embodiments described can be combined or omitted.

What is claimed is:

1. A method of decontaminating surfaces on a living creature comprising:
    generating a beam of electrons with an electron beam generator operating in the range of about 40 kv to 60 kv, the beam of electrons exiting the electron beam generator through an exit window; and
    irradiating the surfaces on the living creature with the beam of electrons, the beam of electrons being of an energy sufficient to decontaminate the surfaces without damaging living tissue.

2. The method of claim 1 further comprising reducing ozone in front of the exit window with an ozone reduction system.

3. The method of claim 2 in which the ozone reduction system comprises a gas removal system, the method further comprising removing ozone generated in front of the exit window with the gas removal system.

4. The method of claim 2 in which the ozone reduction system comprises a nozzle assembly for providing inert gas, the method further comprising supplying the inert gas with the nozzle assembly to occupy an area adjacent to the exit window to prevent the generation of ozone.

5. The method of claim 4 further comprising providing a low density gas as the inert gas to increase the range of the beam of electrons.

6. The method of claim 5 further comprising:
    providing a supply of helium as the low density gas; and
    spacing the exit window of the electron beam generator between about ¼ to 1 inch away from said surfaces.

7. The method of claim 6 further comprising directing the gas in substantially the same direction as the beam of electrons.

8. The method of claim 7 further comprising arranging the nozzle assembly around the exit window.

9. The method of claim 6 further comprising operating the electron beam generator at 50 kv and lower.

10. The method of claim 9 further comprising:
    operating the electron beam generator in the range of 40 kv to 50 kv; and
    spacing the exit window of the electron beam generator between about ¼ to ½ inches away from said surfaces.

11. The method of claim 1 further comprising moving the electron beam generator with a robotic arm for moving the beam of electrons over said surfaces.

12. The method of claim 1 further comprising spacing the exit window from said surfaces with a spacing device.

13. The method of claim 12 further comprising spacing the exit window from said surfaces with a sensor.

14. A method of decontaminating surfaces on a living creature comprising:
    generating beams of electrons from a series of electron beam generators operating in the range of about 40 kv to 60 kv and positioned to simultaneously face multiple surfaces on the living creature with substantially uninterrupted electron beam coverage; and
    simultaneously irradiating the multiple surfaces on the living creature with the beams of electrons, the beams of electrons being of an energy sufficient to decontaminate the surfaces without damaging living tissue.

15. A method of decontaminating surfaces comprising:
    generating a beam of electrons with an electron beam generator, the beam of electrons exiting the electron beam generator through an exit window and irradiating said surfaces;
    reducing ozone in front of the exit window with an ozone reduction system; and
    actively spacing the exit window of the electron beam generator an effective distance away from said surfaces with a spacing device mounted to the electron beam generator.

16. A method of decontaminating surfaces comprising:
    generating a beam of electrons with an electron beam generator operating in the range of about 40 kv to 60 kv, the beam of electrons exiting the electron beam generator through an exit window and irradiating said surfaces;
    providing a supply of low density gas to occupy an area adjacent to the exit window to increase the range of the beam of electrons; and
    spacing the exit window of the electron beam generator between about ¼ to 1 inch away from said surfaces with a spacing device mounted to the electron beam generator.

17. The method of claim 16 further comprising decontaminating surfaces on a living creature.

18. The method of claim 16 further comprising providing a supply of helium as the low density gas.

19. The method of claim 18 further comprising directing the gas in substantially the same direction as the beam of electrons.

20. The method of claim 19 further comprising arranging the nozzle assembly around the exit window.

21. The method of claim 16 further comprising operating the electron beam generator at 50 kv and lower.

22. The method of claim 21 further comprising:
    operating the electron beam generator in the range of 40 kv to 50 kv; and
    spacing the exit window of the electron beam generator between about ¼ to ½ inches away from said surfaces.

23. The method of claim 16 further comprising moving the electron beam generator with a robotic arm for moving the beam of electrons over said surfaces.

24. The method of claim 16 further comprising spacing the exit window from said surfaces with a sensor.

25. A method of decontaminating surfaces on a living creature comprising:
    directing beams of electrons from a series of electron beam generators onto multiple surfaces on a living creature, the beams of electrons exiting the electron beam generators through respective exit windows, the electron beam generators operating in the range of about 40 kv to 60 kv, and configured for simultaneously facing and irradiating the multiple surfaces of the living creature with substantially uninterrupted electron beam coverage; and
    providing a supply of low density gas to occupy areas adjacent to the exit windows to increase the range of the beams of electrons.

26. A decontamination apparatus comprising:
an electron beam generator operating in the range of about 40 kv to 60 kv for generating a beam of electrons to decontaminate surfaces, the beam of electrons exiting the electron beam generator through an exit window;
a nozzle assembly for providing a supply of low density gas for occupying an area adjacent to the exit window to increase the range of the beam of electrons; and
a spacing device mounted to the electron beam generator for spacing the exit window of the electron beam generator between about ¼ to 1 inch away from said surfaces.

27. The apparatus of claim 26 in which the low density gas is helium.

28. The apparatus of claim 27 in which the nozzle assembly directs the gas in substantially the same direction as the beam of electrons.

29. The apparatus of claim 28 in which the nozzle assembly is arranged around the exit window.

30. The apparatus of claim 26 in which the electron beam generator operates at 50 kv and lower.

31. The apparatus of claim 30 in which the electron beam generator operates in the range of 40 kv to 50 kv and the spacing device spaces the exit window of the electron beam generator between about ¼ to ½ inches away from said surfaces.

32. The apparatus of claim 26 in which said surfaces are on a living creature.

33. The apparatus of claim 26 further comprising a robotic arm to which the electron beam generator is mounted for moving the beam of electrons over said surfaces.

34. The apparatus of claim 26 in which the spacing device is a sensor.

35. A decontamination apparatus comprising:
at least one electron beam generator operating in the range of about 40 kv to 60 kv for generating at least one beam of electrons to decontaminate surfaces, the at least one beam of electrons exiting the at least one electron beam generator through at least one exit window;
at least one nozzle assembly for providing a supply of low density gas for occupying an area adjacent to the at least one exit window to increase the range of the at least one beam of electrons;
a spacing device mounted to the electron beam generator for spacing the at least one exit window of the at least one electron beam generator between about ¼ to 1 inch away from said surfaces; and
a robotic arm for moving the at least one beam of electrons over said surfaces.

36. The apparatus of claim 35 which said surfaces are on a living creature.

37. The apparatus of claim 36 in which the low density gas is helium.

38. The apparatus of claim 37 in which the at least one electron beam generator operates in the range of 40 kv to 50 kv and the spacing device spaces the at least one exit window about ¼ to ½ inches away from said surfaces.

39. The apparatus of claim 38 in which the spacing device is a sensor.

40. A decontamination apparatus comprising:
a series of electron beam generators operating in the range of about 40 kv to 60 kv for generating beams of electrons to decontaminate multiple surfaces of a living creature, the beams of electrons exiting the electron beam generators through respective exit windows, the electron beam generators being configured for simultaneously facing and irradiating the multiple surfaces of the living creature with substantially uninterrupted electron beam coverage; and
a nozzle assembly for providing a supply of low density gas for occupying areas adjacent to the exit windows to increase the range of the beams of electrons.

41. A decontamination apparatus comprising:
an electron beam generator for generating a beam of electrons to decontaminate surfaces, the beam of electrons exiting the electron beam generator through an exit window;
an ozone reduction system for reducing ozone in front of the exit window; and
a spacing device mounted to the electron beam generator for actively spacing the exit window of the electron beam generator within an effective distance away from said surfaces.

42. The apparatus of claim 41 in which the ozone reduction system comprises a gas removal system.

43. The apparatus of claim 41 in which the ozone reduction system comprises a nozzle assembly for providing inert gas to occupy an area adjacent to the exit window to prevent the generation of ozone.

44. The apparatus of claim 43 in which the inert gas is a low density gas to increase the range of the beam of electrons.

45. The apparatus of claim 44 in which the low density gas is helium, the electron beam generator operating in the range of about 40 kv to 60 kv, with the exit window of the electron beam generator being spaced between about ¼ to 1 inch away from said surfaces.

46. A method of treating surfaces comprising:
generating a beam of electrons with an electron beam generator, the beam of electrons exiting the electron beam generator through an exit window for irradiating the surfaces;
moving the electron beam generator over the surfaces with a robotic arm in a manner for obtaining continuous area irradiation coverage over the surfaces; and
controllably spacing the exit window of the electron beam generator a desired distance away from the surfaces with a spacing device mounted to the electron beam generator as the electron beam generator is moved over the surfaces.

47. The method of claim 46 further comprising continuously and actively spacing the exit window of the electron beam generator the desired distance away from the surfaces.

48. The method of claim 46 further comprising hermetically sealing the electron beam generator.

49. The method of claim 46 further comprising treating the surfaces for any of sterilization, curing and facilitating chemical reactions.

50. An apparatus for treating surfaces comprising:
an electron beam generator for generating a beam of electrons, the beam of electrons exiting the electron beam generator through an exit window for irradiating the surfaces; and
a robotic arm for moving the electron beam generator over the surfaces in a manner to obtain continuous area irradiation coverage over the surfaces, with a spacing device mounted to the electron beam generator, the robotic arm is capable of controllably spacing the exit window of the electron beam generator a desired distance away from the surfaces as the electron beam generator is moved over the surfaces.

51. The apparatus of claim 50 in which the robotic arm is capable of continuously and actively spacing the exit window of the electron beam generator the desired distance away from the surfaces.

52. The apparatus of claim 50 in which the electron beam generator is hermetically sealed.

53. The apparatus of claim 50 in which treating the surfaces includes any of sterilization, curing and facilitating chemical reactions.

54. An apparatus for treating surfaces comprising:

an electron beam generator for generating a beam of electrons, the beam of electrons exiting the electron beam generator through an exit window for irradiating the surfaces; and a robotic device for moving the beam of electrons over the surfaces in a manner to obtain continuous area irradiation coverage over the surfaces, the exit window being spaced from said surfaces with a spacing device mounted to the electron beam generator.

55. A method of treating surfaces comprising:

generating a beam of electrons with an electron beam generator, the beam of electrons exiting the electron beam generator through an exit window for irradiating the surfaces;

moving the beam of electrons over the surfaces with a robotic device in a manner for obtaining continuous area irradiation coverage over the surfaces; and spacing the exit window from said surfaces with a spacing device mounted to the electron beam generator.

* * * * *